(12) United States Patent
Yokoyama

(10) Patent No.: US 11,318,281 B2
(45) Date of Patent: May 3, 2022

(54) CATHETER FOR EXTRACORPOREAL BLOOD CIRCULATOR

(71) Applicant: TERUMO KABUSHIKI KAISHA, Tokyo (JP)

(72) Inventor: Kenji Yokoyama, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 339 days.

(21) Appl. No.: 16/668,138

(22) Filed: Oct. 30, 2019

(65) Prior Publication Data

US 2020/0069909 A1 Mar. 5, 2020

Related U.S. Application Data

(63) Continuation of application No. PCT/JP2018/010883, filed on Mar. 19, 2018.

(30) Foreign Application Priority Data

Jun. 9, 2017 (JP) .............................. JP2017-114672

(51) Int. Cl.
*A61M 25/00* (2006.01)
*A61M 1/36* (2006.01)

(52) U.S. Cl.
CPC ........ *A61M 25/003* (2013.01); *A61M 1/3607* (2014.02); *A61M 25/007* (2013.01); *A61M 2025/0031* (2013.01)

(58) Field of Classification Search
CPC .. A61M 2025/0031; A61M 2025/0039; A61M 25/003; A61M 25/007; A61M 1/3607; A61M 1/3659; A61M 1/3661
See application file for complete search history.

(56) References Cited

U.S. PATENT DOCUMENTS

| 4,098,275 | A | * | 7/1978 | Consalvo | ............ | A61M 5/1582 604/6.05 |
| 4,134,402 | A | * | 1/1979 | Mahurkar | ........... | A61M 5/1582 604/248 |
| 5,976,114 | A | * | 11/1999 | Jonkman | ............. | A61M 1/3659 604/264 |
| 7,748,275 | B2 | | 7/2010 | Kouda et al. | | |
| 2005/0182352 | A1 | | 8/2005 | DiMatteo et al. | | |
| 2006/0020256 | A1 | * | 1/2006 | Bell | .................. | A61M 25/0045 604/523 |

FOREIGN PATENT DOCUMENTS

JP 2001104486 A 4/2001

OTHER PUBLICATIONS

International Search Report, PCT/JP2018/010883, dated May 9, 2018.

* cited by examiner

*Primary Examiner* — James D Ponton
(74) *Attorney, Agent, or Firm* — MacMillan, Sobanski & Todd, LLC

(57) ABSTRACT

A catheter for an extracorporeal blood circulator disperses a flow of blood flowing out from a blood feeding hole to reduce the impact of blood collision on a living organ. The catheter 60 includes a blood feeding lumen 61 extending in an axial direction and a blood feeding hole 63 communicating with a distal end of the blood feeding lumen, and a side portion 63a of the blood feeding hole on the proximal side facing the blood feeding lumen is cut out to a bottom portion 63b of the blood feeding hole.

9 Claims, 10 Drawing Sheets

CATHETER FOR EXTRACORPOREAL BLOOD CIRCULATOR

CROSS REFERENCE TO RELATED APPLICATIONS

This application is a continuation of PCT Application No. PCT/JP2018/010883, filed Mar. 19, 2018, based on and claiming priority to Japanese Application No. 2017-114672, filed Jun. 9, 2017, both of which are incorporated herein by reference in their entirety.

BACKGROUND OF THE INVENTION

The present invention relates to a catheter provided with a blood feeding hole for feeding blood to a living body.

Conventionally, in order to provide cardiopulmonary resuscitation, circulatory support, and respiratory support in emergency treatment, treatment with percutaneous cardiopulmonary support (PCPS) has been performed. Percutaneous cardiopulmonary support is a method of temporarily assisting and covering cardiopulmonary function using an extracorporeal circulator. In addition, the extracorporeal circulator is also used in open-heart surgery as well.

The extracorporeal circulator has an extracorporeal circulation circuit including a centrifugal pump, an artificial lung (oxygenator), a blood removing path, a blood feeding path, and the like, and is configured to perform gas exchange on removed blood and feed the blood to the blood feeding path. U.S. Pat. No. 7,748,275 B2, for example, describes a circulation circuit in an extracorporeal circulator.

In such circulation circuits, a blood feeding catheter provided with a blood feeding hole (outflow hole) is used to send blood after gas exchange to a desired position in the living body. Typically, a diameter of the blood feeding hole of the catheter is smaller than an inner diameter of a blood vessel. Therefore, a flow rate of the blood flowing out from the blood feeding hole becomes relatively high, and the blood may flow out linearly sharply from the blood feeding hole. In this case, the blood may intensively collide with a part of a living organ (such as a cardiac wall or a vascular wall).

In order to solve the above-mentioned problems, it is an object of the invention to provide a catheter that can disperse the outflow of blood from a blood feeding hole to reduce the impact of blood collision on a living organ.

SUMMARY OF THE INVENTION

To achieve the above-described object, there is provided a catheter extending in an axial direction for allowing passage of blood, the catheter including: a blood feeding lumen extending in the axial direction; and a blood feeding hole communicating with a distal end of the blood feeding lumen, wherein a side portion of the blood feeding hole on a proximal side facing the blood feeding lumen is cut out to a bottom portion of the blood feeding hole.

In the catheter configured as described above, the blood flowing through the blood feeding lumen reaches the blood feeding hole formed at the distal end of the blood feeding lumen and then flows out of the blood feeding hole while being dispersed to the outside. Therefore, the catheter according to the present invention can reduce the impact on the living organ caused by the collision of the blood flowing out from the blood feeding hole.

DETAILED DESCRIPTION OF PREFERRED EMBODIMENTS

Referring now to the attached drawings, embodiments of the invention will be described. Note that the following description is not intended to limit the technical scope or significance of terms described in Claims. In some cases, the dimensional ratios of drawings are exaggerated for the convenience of illustration and may be different from the actual ratios.

Figure 1:
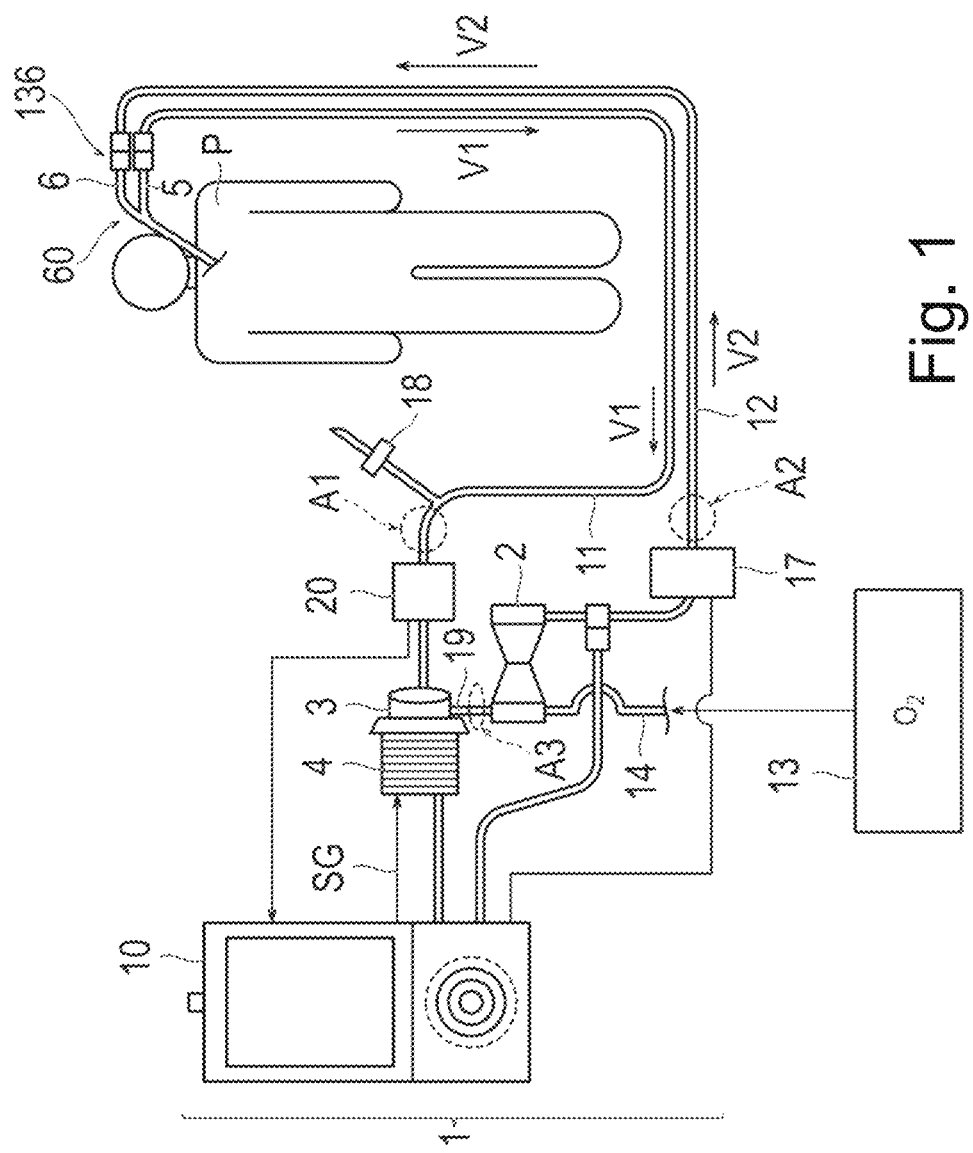
FIG. 1 is a system diagram illustrating an example of an extracorporeal circulator to which a catheter according to an embodiment is applied.

FIG. 1 is a diagram illustrating an example of an extracorporeal circulator to which a catheter according to an embodiment of the invention is applied. The extracorporeal circulator can be used when a patient's heart is weakened, for example, for percutaneous cardiopulmonary support (PCPS), which supports and covers functions of the heart and lung temporarily until a cardiac function is restored.

An extracorporeal circulator 1 may be applied to a procedure of a Veno-Venous (VV) method. The VV method includes activating a pump to remove blood from patient's vein (for example, vena cava), performing gas exchange of blood by an artificial lung for oxygenation of blood, and then returning the blood back to the patient's vein (for example, vena cava) again. In this manner, the extracorporeal circulator 1 can be used as a device for supporting the patient's heart and lung.

As illustrated in FIG. 1, the extracorporeal circulator 1 includes a circulation circuit for circulating blood. The circulation circuit includes an artificial lung 2, a centrifugal pump 3, a drive motor 4, which is driving means for driving the centrifugal pump 3, a catheter 60, and a controller 10 as a control unit.

Figure 3:
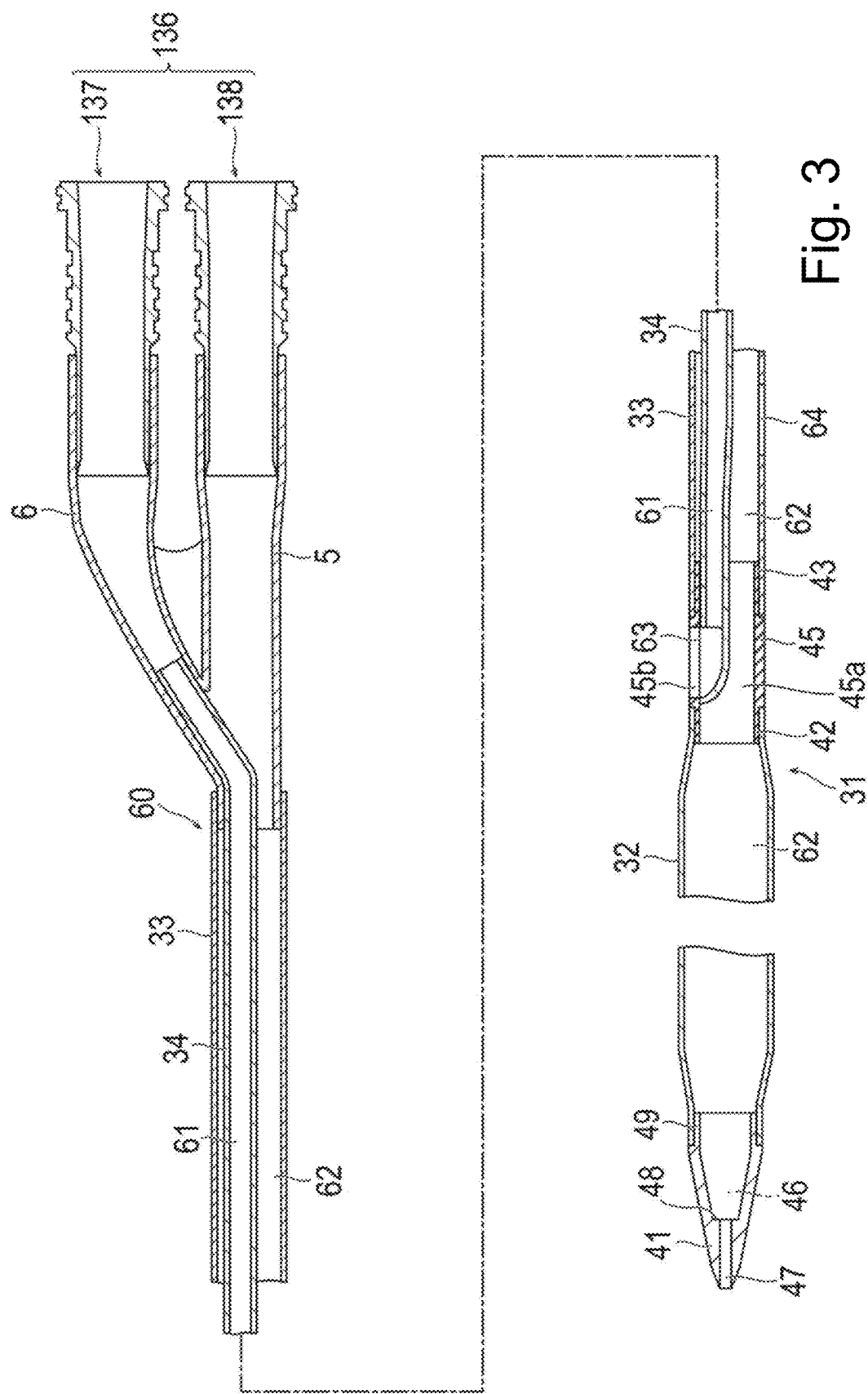
FIG. 3 is a cross-sectional view illustrating the catheter according to the embodiment.

At a proximal side of the catheter 60, a blood removing tube 5 and a blood feeding tube 6 are disposed (see FIG. 3).

The blood removing tube 5 includes a blood removing lumen in communication with a blood removing lumen 62 (see FIG. 3) in the catheter 60. The blood feeding tube 6 includes a blood feeding lumen in communication with a blood feeding lumen 61 (see FIG. 3) in the catheter 60.

The catheter 60 is inserted, for example, from an internal jugular vein at a neck, passes through a superior vena cava and a right atrium, and a distal side of the catheter 60 is indwelled in an inferior vena cava. A blood feeding target of the catheter 60 is, for example, a right atrium. Blood removal targets of the catheter 60 are two points; the internal jugular vein (or the superior vena cava) and the inferior vena cava.

The blood removing tube 5 is connected to the centrifugal pump 3 via a blood removing tube (blood removal line) 11. The blood removing tube 11 is a pipe line for feeding blood.

The artificial lung 2 is disposed between the centrifugal pump 3 and a blood feeding tube 12. The blood feeding tube 12 is a pipe line that connects the artificial lung 2 and the blood feeding tube 6.

The blood flows in a V1 direction in FIG. 1 in the blood removing tube 11. In addition, the blood flows in a V2 direction in FIG. 1 in the blood feeding tube 12.

The blood removing tube 11 and the blood feeding tube 12 may be, for example, tubular members made of a flexible synthetic resin having a high transparency and a resiliently deformable property such as a vinyl chloride resin or a silicone rubber.

The drive motor 4 actuates the centrifugal pump 3 based on a command SG of the controller 10. The centrifugal pump 3 passes the blood removed from the blood removing tube 11 through the artificial lung 2, and then returns the blood to a patient P through the blood feeding tube (the blood feeding line) 12.

The artificial lung 2 performs gas exchange (addition of oxygen and/or removal of carbon dioxide) for blood. For example, a membrane type artificial lung, particularly preferably a hollow fiber membrane type artificial lung may be used as the artificial lung 2.

Oxygen gas is fed from an oxygen gas supply unit 13 to the artificial lung 2 via a tube 14.

The circulation circuit illustrated in FIG. 1 includes an ultrasound air bubble detection sensor 20 disposed midway through the blood removing tube 11 and a fast clamp 17 disposed midway through the blood feeding tube 12.

When air bubbles enter into the circulation circuit due to an erroneous operation of a three-way stopcock 18 or breakage of the tube during the extracorporeal circulation, the ultrasound air bubble detection sensor 20 detects the air bubbles entered therein.

When the ultrasound air bubble detection sensor 20 detects that air bubbles are present in blood fed into the blood removing tube 11, the ultrasound bubble detection sensor 20 transmits a predetermined detection signal to the controller 10. The controller 10 notifies a warning by an alarm based on the detection signal, and lowers the number of rotation of the centrifugal pump 3 or stops the centrifugal pump 3. In addition, the controller 10 transmits an action command to the fast clamp 17, and the fast clamp 17 blocks the blood feeding tube 12. Accordingly, the air bubbles are prevented from being delivered to the body of the patient P.

A predetermined pressure sensor (not illustrated) is disposed in the extracorporeal circulator 1.

The pressure sensor may be mounted at at least one of a mounting position A1 on the blood removing tube 11, a mounting position A2 on the blood feeding tube 12, and a mounting position A3 of a connecting tube 19 connecting the centrifugal pump 3 and the artificial lung 2. When the extracorporeal circulation is performed for the patient P by the extracorporeal circulator 1, the pressure sensor measures the pressures in the respective tubes 11, 12, 19.

Next, a catheter assembly 100 according to the present embodiment will be described.

Figure 2:
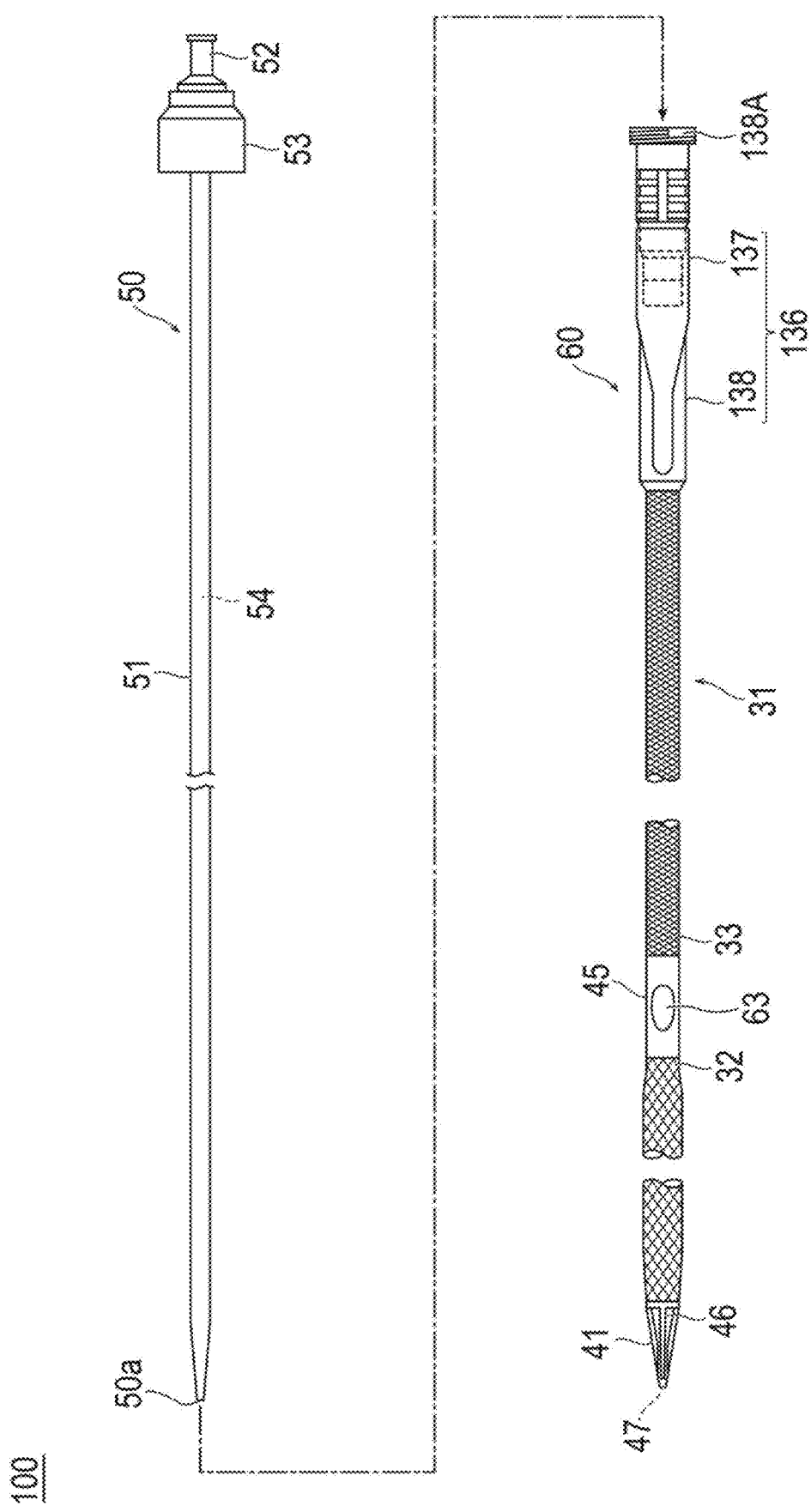
FIG. 2 is a top view illustrating a catheter assembly according to the embodiment.

The catheter assembly 100 includes the catheter 60 configured to pass blood and a dilator 50 to be inserted into the catheter 60 as illustrated in FIG. 2. Note that the catheter 60 can be used as the catheter 60 described with reference to FIG. 1.

In this specification, a side of the catheter 60 to be inserted into the living body is referred to as "distal side", and a hand-side where a user such as an operator operates is referred to as "proximal side". Note that the distal end portion implies a certain range including a distal end (distal-most end) and a periphery thereof, and a proximal portion indicates a certain range including a proximal end (proximal-most end) and a periphery thereof. In FIGS. 5 to 8, an axial direction of the catheter 60 is indicated by an arrow X, and orthogonal directions intersecting the axial direction X are indicated by arrows Y and Z, respectively.

As illustrated in FIG. 3, the catheter 60 includes a blood feeding lumen 61 and a blood removing lumen 62. The catheter 60 is a so-called double lumen catheter capable of simultaneously performing both blood feeding by the blood feeding lumen 61 and blood removal by the blood removing lumen 62.

As illustrated in FIG. 3, the catheter 60 has a first tube 32 disposed at the distal side, a second tube 33 disposed closer to the proximal side than the first tube 32, a third tube 34 inserted into the second tube 33, a connector 45 that connects the first tube 32 and the second tube 33, a distal end tip 41 disposed at the distal end of the first tube 32, and a lock connector 136 disposed at the proximal end of the catheter 60.

As shown in FIG. 3, the blood feeding lumen 61 is formed in a lumen of the third tube 34. The blood removing lumen 62 is formed within the lumen of the first tube 32, the second tube 33, and the connector 45.

For inserting the catheter 60 in a living body, an operator such as a surgeon uses the dilator 50 illustrated in FIG. 2. Specifically, the dilator 50 is inserted through the blood removing lumen 62 of the catheter 60, and the catheter assembly 100 is inserted into the living body in a state in which the catheter 60 and the dilator 50 integrated. Note that the procedure for using the catheter 60 will be described later.

Next, the configuration of each part of the catheter 60 will be described.

As illustrated in FIGS. 2 and 3, the catheter 60 includes a catheter tube 31 that constitutes a main body portion of the catheter 60. The catheter tube 31 has the first tube 32, the second tube 33, and the third tube 34.

The first tube 32 is configured to have a higher elasticity than the second tube 33. The first tube 32 is configured such that an outer diameter and an inner diameter are greater than the second tube 33 in a state in which the dilator 50 is not inserted through the catheter tube 31.

As illustrated in FIG. 3, the second tube 33 includes a blood removing hole 64 communicating with the blood removing lumen 62. The blood removing hole 64 can be formed in an elliptical shape in plan view, for example. The blood removing hole 64 may also be configured by a hole (side hole) formed by cutting out only a part of the second tube 33 in the circumferential direction, for example.

The first tube 32 and the second tube 33 can be formed, for example, to have sufficient lengths (axial length) to place each of through-holes 46 and 47 (see FIGS. 2 and 3) of the distal end tip 41 and the blood removing hole 64 of the second tube 33 into the living organs as blood removal targets.

The catheter 60 may, for example, be positioned with the first tube 32 in the inferior vena cava, which is relatively thick vessel, and the second tube 33 in the internal jugular vein, which is a relatively thin blood vessel with the dilator 50 inserted. In this case, each of the through-holes 46 and 47 of the distal end tip 41 disposed at the distal end of the first tube 32 can be disposed in the inferior vena cava which is a blood removal target, and the blood removing hole 64 of the second tube 33 can be disposed in the internal jugular vein, which is a blood removal target.

When the catheter 60 is placed (indwelled) as described above for use, the first tube 32 can be formed to have the length ranging, for example, from 20 to 40 cm, and the second tube 33 can be formed to have the length ranging, for example, from 20 cm to 30 cm.

Figure 4:
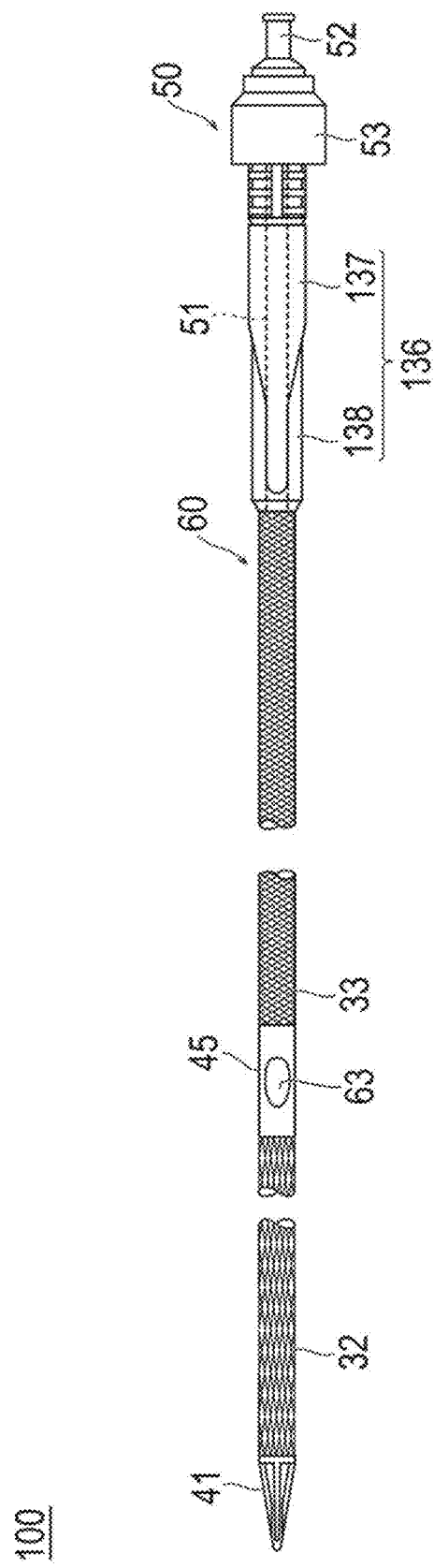
FIG. 4 is a top view of the catheter assembly in a state in which a dilator is inserted into an interior of the catheter.

As illustrated in FIG. 4, when the dilator 50 is inserted into the blood removing lumen 62 in the catheter 60, the first tube 32, which is highly elastic, extends in the axial direction. The outer diameter and the inner diameter of the first tube 32 become smaller with the extension (i.e., stretching) in the axial direction. At this time, the outer diameter of the first tube 32 becomes substantially the same as the outer diameter of the second tube 33. Since the operator such as a surgeon inserts the catheter 60 into the living body in a state in which the first tube 32 is extended in the axial direction and thus the outer diameter and the inner diameter are reduced, minimally invasive insertion of the catheter 60 is achieved.

In addition, when the dilator 50 is removed from the catheter 60 after the catheter 60 is indwelled in the living body, the first tube 32 is contracted from the axially extended state and thus the outer diameter and the inner diameter of the first tube 32 increase. As described above, the first tube 32 here is placed in the inferior vena cava, which is a relatively thick blood vessel. Therefore, when the first tube 32 is inserted into the inferior vena cava and the dilator 50 is removed from the catheter 60, the first tube 32 is deformed so that the outer diameter of the first tube 32 increases in order to contact the inner diameter of the inferior vena cava, and the inner diameter of the first tube 32 increases accordingly.

Here, the pressure loss of blood flowing in the blood removing lumen 62 of the first tube 32 can be reduced by increasing the inner diameter of the first tube 32. By reducing the pressure loss of the blood removing lumen 62 of the first tube 32, the flow rate of the blood flowing through the circulation circuit can be increased. Therefore, in order to obtain a sufficient amount of circulation of blood, it is preferable to increase the inner diameter of the first tube 32. However, when the inner diameter of the first tube 32 is increased in a state in which a thickness is maintained constant, the outer diameter of the first tube 32 is increased. Therefore, when the catheter 60 is inserted into the living body, a burden on the patient is increased, which impairs the minimally invasive procedure.

From the viewpoints as described above, the inner diameter of the first tube 32 may be, for example, ranged from 9 mm to 11 mm, and the inner diameter of the second tube 33 may be, for example, ranged from 4 mm to 8 mm. In addition, the thickness of the first tube 32 and the second tube 33 may be ranged, for example, from 0.4 mm to 0.5 mm.

As illustrated in FIGS. 2 and 3, in the state in which no dilator 50 is inserted into the catheter 60, the distal end portion of the first tube 32 has a tapered part gradually tapering toward the distal side in the axial direction. Similarly, the proximal portion of the first tube 32 has a tapered part gradually tapered toward the proximal side in the axial direction. The inner diameter of the distal end portion of the first tube 32 is changed so as to be continuous with the inner diameter of the distal end tip 41 disposed at the distal side thereof. The inner diameter of the proximal portion of the first tube 32 changes to be continuous with the inner diameter of the connector 45 disposed at the proximal side thereof.

The first tube 32 and the second tube 33 include, for example, a reinforcement body made of a wire braided in an intersecting manner, and a resin layer provided so as to cover the reinforcement body.

The wire used for the reinforcement body may be formed of, for example, a shape memory material such as a known shape memory metal or a shape memory resin. The shape memory metal that may be used here includes, for example, titanium-based (Ni—Ti, Ti—Pd, Ti—Nb—Sn, etc.) or copper-based alloy. The shape memory resin includes, for example, acrylic resin, transisoprene polymer, polynorbornene, styrene-butadiene copolymer, and polyurethane.

Since the wire used for the reinforcement body is made of the shape memory material as described above, the first tube 32 and the second tube 33 are configured in such a manner that an amount of deformation of the first tube 32 in the axial direction when the dilator 50 is removed from the catheter 60 (an axial contraction distance) and an amount of deformation of the first tube 32 in the axial direction when the dilator 50 is inserted through the catheter 60 (an axial extension distance) are substantially the same.

As illustrated in FIG. 2, the wire forming the reinforcement body of the first tube 32 can be formed, for example, such that spacing between the weaving becomes coarser than the wire forming the reinforcement body of the second tube 33 (the weaving spaces increase). In this configuration, since the first tube 32 is increased in flexibility compared to the second tube 33, axial stretching property is improved.

A wire diameter that forms the reinforcement body of each of the tubes 32 and 33 ranges, for example, from 0.1 mm to 0.2 mm.

A resin layer of the first tube 32 is made of, for example, a soft material lower in hardness than a resin layer of the second tube 33. In this configuration, the first tube 32 is further enhanced in flexibility compared to the second tube 33.

The resin layers of each of the tubes 32 and 33 can be formed of, for example, vinyl chloride, silicon, polyethylene, nylon, urethane, polyurethane, fluorine resin, thermoplastic elastomer resin, or the like, or a composite material thereof.

The silicon materials have high biocompatibility and are soft by themselves. Therefore, the silicon materials have a characteristic that they can hardly damage the blood vascular wall and cardiac wall. The polyethylene materials are soft and have a hardness that is resistant to pressure. In addition, the polyethylene materials have biocompatibility comparable to that of the silicon materials. The polyethylene materials are harder than silicon and have a characteristic that they are easy to insert into thin blood vessels. The polyurethane materials have a characteristic that it becomes softer after insertion into the living body. As the material for forming the resin layer of each of the tubes 32 and 33, any suitable material can be selected appropriately, taking into account the characteristics of each material as described above.

Note that when the resin layer is made of polyurethane material, a hydrophilic coating may be applied to the resin layer. By applying the above-described coating, the tube surface becomes smooth, and it makes insertion into blood vessels easy, so that the vascular wall is less likely to be damaged. In addition, probability of adhesion of blood or protein is low, and prevention of formation of blood clots is expected.

The method of forming each of the tubes 32 and 33 is not specifically limited, but may be formed by, for example, dip coating (immersion method) or insert molding.

Next, the third tube 34 and the connector 45 will be described.

As illustrated in FIG. 3, the third tube 34 is inserted into the blood removing lumen 62 of the second tube 33 and a lumen 45a of the connector 45. Preferably, the third tube 34 may have a tubular, semi-cylindrical shape in which a planar bottom wall of third tube 34 generally extends along a central diameter of second tube 33 and a curved upper wall of third tube 34 generally extends along aside wall of second tube 33. A blood feeding hole 63 communicating with the blood feeding lumen 61 is formed at the distal end of the blood feeding lumen 61 of the third tube 34.

The length (axial length) of the third tube 34 can be formed to be longer than the length (axial length) of the second tube 33, for example. The length of the third tube 34 can be, for example, 15 cm to 25 cm. A cross-sectional area of the third tube 34 may be formed to be ranged, for example, from 11 mm2 to 15 mm2.

The third tube 34 may be made of vinyl chloride, silicon polyethylene, nylon, urethane, polyurethane, fluorine resin, thermoplastic elastomer resin, or the like, or may be made using a composite material thereof.

As illustrated in FIG. 3, the connector 45 is a joint member connecting the first tube 32 and the second tube 33. The connector 45 can be formed of, for example, a structure (housing) that has a constant (i.e., rigid) shape. The connector 45 may be made of, for example, a hard plastic.

Connection sections 42 and 43 are formed on each of the both ends of the tubular main body portion of the connector 45. The connection section 42 of the connector 45 on a distal side thereof is inserted into a proximal side of the first tube 32, and the connection section 43 on the proximal side is inserted into the distal side of the second tube 33. The lumen 45a of the connector 45 communicates with the blood removing lumen 62 on the first tube 32 side and the blood removing lumen 62 on the second tube 33 side.

The connector 45 has a side hole 45b that opens into a part of a side surface along the circumferential direction of the connector 45. The blood feeding hole 63 of the third tube 34 is disposed so as to face the side hole 45b of the connector 45. The blood feeding hole 63 and the side hole 45b cooperatively define an opening allowing blood flow from third tube 34 to exit the catheter 60.

Next, referring to FIGS. 5 to 8, the blood feeding hole 63 provided on the third tube 34 will be described.

The blood feeding hole 63 (i.e., the shaped distal end) of the third tube 34 allows the blood passing through the blood feeding lumen 61 of the third tube 34 to flow out of the catheter 60. Specifically, the operator such as a doctor feeds blood to the living body by causing the blood oxygenated by the artificial lung 2 to flow out of the blood feeding hole 63 while the blood feeding hole 63 is positioned in the vicinity of the blood feeding target (e.g., the right atrium) of the living body. As used herein, "blood feeding hole" refers to the walls and shaped end opening of third tube 34 that cooperates with side hole 45b of connector 45 to guide a flow of blood into the living body.

Figure 6:
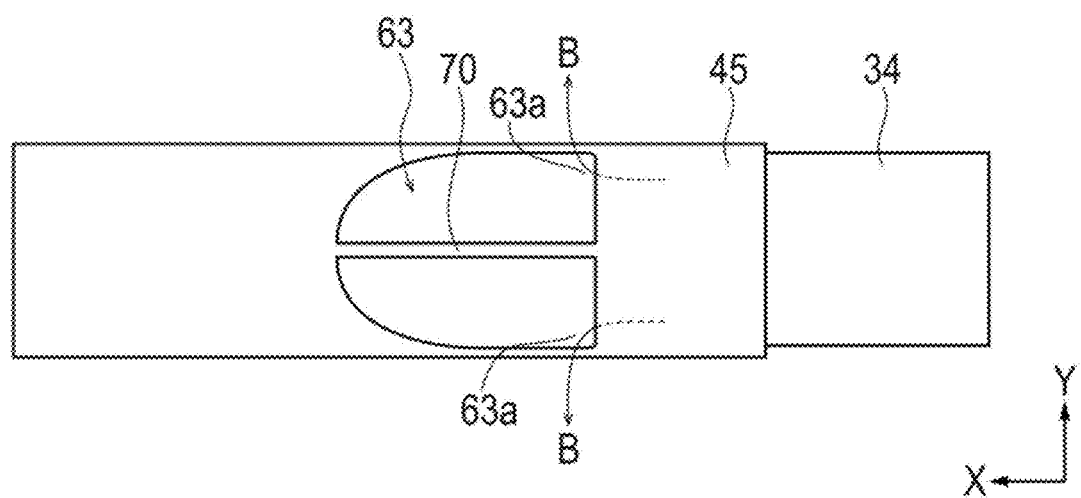
FIG. 6 is a plan view viewed from a direction of an arrow 6A illustrated in FIG. 5.

The blood feeding hole 63 has an outer shape decreasing gradually in width from the proximal side to the distal side, in plan view illustrated in FIG. 6. The blood feeding hole 63 is formed by a side hole formed by cutting out part of the side surface (i.e., curved upper wall) along the circumferential direction of the third tube 34 while the planar bottom wall of the third tube 34 bends upward to form a concave end as described below.

Figure 5:
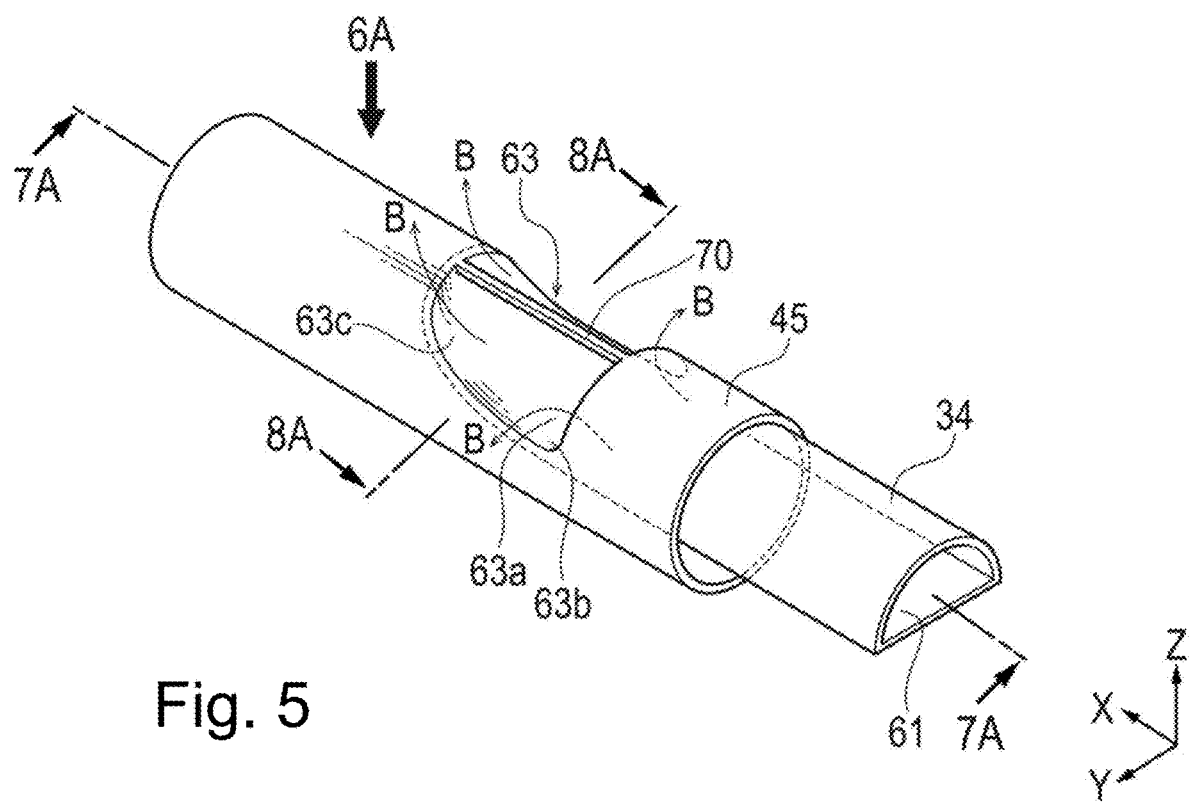
FIG. 5 is a perspective view illustrating a vicinity of a blood feeding hole of the catheter according to the embodiment in an enlarged scale.
Figure 7:
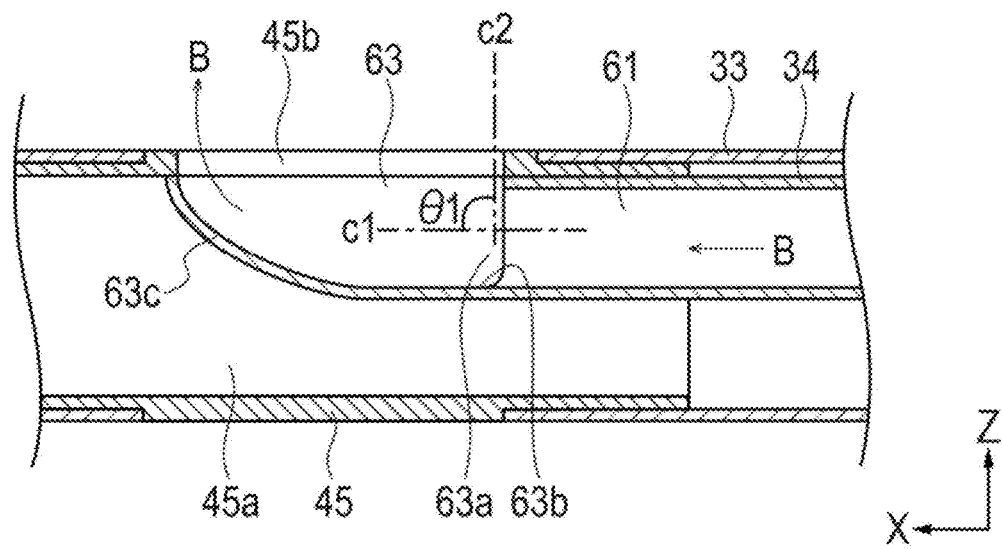
FIG. 7 is a cross-sectional view taken along a line 7A-7A in FIG. 5.

As illustrated in FIGS. 5 and 7, a proximal side portion 63a of the blood feeding hole 63 facing the blood feeding lumen 61 is cut out to a bottom portion 63b of the blood feeding hole 63, so that side portion 63a define a proximal edge of the blood feeding hole 63 that is substantially perpendicular to the axis X. In other words, the vicinity of the proximal end of the blood feeding hole 63 is not surrounded by a wall portion (i.e., upper curved tube wall) of the third tube 34 and is opened outside the catheter 60 over a range of the circumferential direction in which the blood feeding hole 63 is formed.

Note that in the cross section along the axial direction illustrated in FIG. 7, an angle θ1 formed by a straight line c1 parallel to the axis of the catheter 60 and a straight line c2 parallel to an opening surface on the proximal side of the blood feeding hole 63 can be set to an angle of, for example, 90° or to an angle within a few degrees of 90°.

As illustrated in FIGS. 5 and 6, a distal wall 63c curved into a concave shape toward the distal end in the axial direction is formed on the distal side of the blood feeding hole 63 (as an extension of the bottom planar wall of the third tube 34).

The distal wall 63c adjusts a direction of the blood flowing to the distal side of the blood feeding hole 63 in a predetermined direction (e.g., in a direction of a tricuspid valve in a case where the blood feeding hole 63 is positioned in the right atrium). In addition, the distal wall 63c can reduce the force of the blood flow by contacting the blood flowing linearly to the distal side of the blood feeding hole 63 so that it can prevent the blood from sharply flowing to the distal side of the blood supply hole 63.

It should be noted that the specific shape of the distal wall 63c (e.g., the cross-sectional shape illustrated in FIG. 7) and the axial length are not particularly limited, and can be appropriately changed.

The flow (indicated by an arrow B in FIGS. 5 to 8) of the blood flowing out from the blood feeding hole 63 will be described.

As illustrated in FIGS. 5 and 6, the blood flowing through the blood feeding lumen 61 of the third tube 34 is spread and dispersed outside the blood feeding hole 63 without being obstructed by the wall of the third tube 34 when the blood reaches the blood feeding hole 63. Therefore, the shock generated when the blood flowing out from the blood feeding hole 63 comes into contact with the cardiac wall or the like can be lessened. The blood flows along the distal wall 63c when it reaches the distal wall 63c formed at the distal side of the blood feeding hole 63. Accordingly, an outflow direction of the blood flowing out from the distal side of the blood feeding hole 63 can be guided in a predetermined direction.

Figure 8:
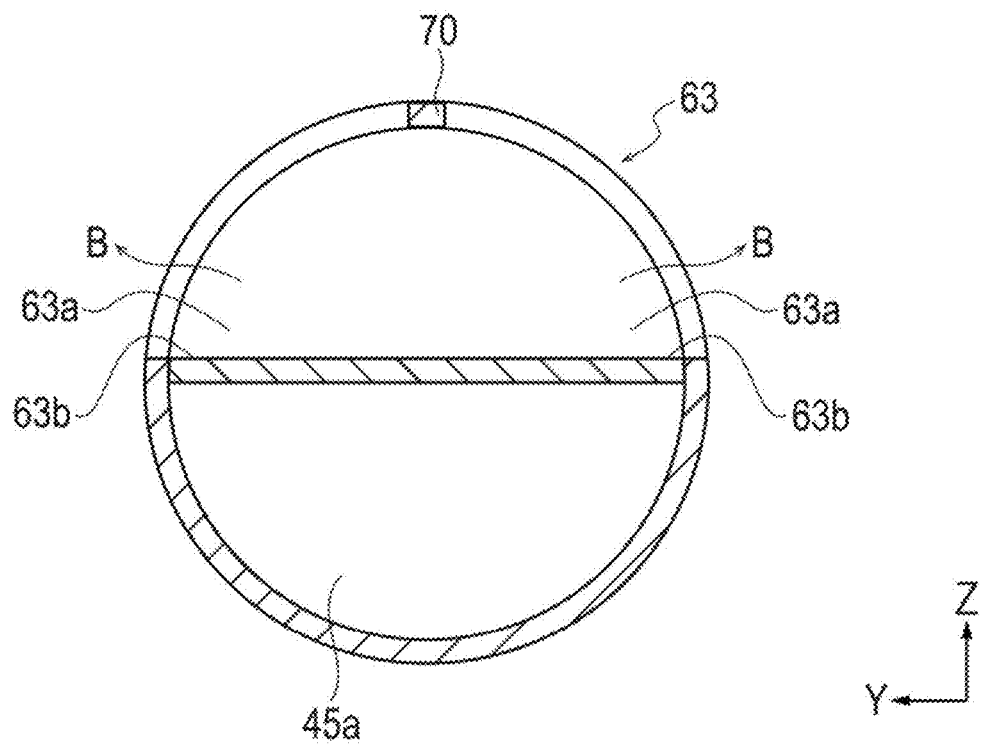
FIG. 8 is a cross-sectional view taken along a line 8A-8A in FIG. 5.

As illustrated in FIGS. 6 and 8, the third tube 34 is provided with a rib 70 extending between the distal side of the blood feeding hole 63 and the proximal side of the blood feeding hole 63.

The rib 70 can be formed of a rod-like member extending substantially linearly along the axial direction, formed by a portion of the connector 45 extended across side hole 45b, as illustrated in FIG. 6, for example. The rib 70 has a function to prevent the biological tissue (such as the wall of the blood vessel) from being caught by the blood feeding hole 63 when the catheter 60 is inserted into the living body. In other words, the rib 70 prevents the biological tissue from falling into the blood feeding hole 63 by supporting the biological tissue in contact with the rib 70.

As illustrated in FIG. 8, the rib 70 can be disposed at a substantially central position in a width direction (left and right directions in FIG. 8), for example, on the cross section of the blood feeding hole 63. Since the rib 70 is disposed in such a location, the biological tissue is preferably prevented from being caught by the blood feeding hole 63 even when a plurality of ribs are not provided. Note that the cross sectional shape of the outer surface of the rib 70 can be curved into a convex shape toward the outside, for example, in order to preferably prevent the occurrence of a catch or the like in the biological tissue.

The rib 70 is not particularly limited in shape (thickness, length, cross-sectional shape, etc.), number, arrangement (linear arrangement, curved arrangement, etc.), material, and so on, as long as the above-described effects are exhibited. The ribs 70 may be formed integrally by a part of the third tube 34, or may be formed of a separate member from the third tube 34.

Next, the distal end tip 41 and the lock connector 136 will be described.

As illustrated in FIG. 3, the distal end tip 41 is disposed at a distal end of the first tube 32. The distal end tip 41 is provided with a tapered shape decreasing in diameter as it goes toward the distal side.

Inside the distal end tip 41 is formed a flat receiving surface 48, which is in contact with a flat surface 50a (see FIG. 2) formed at the distal end of the dilator 50.

As illustrated in FIG. 3, the distal end tip 41 includes a base portion 49 to be inserted to the distal end of the first tube 32, a plurality of the through-holes 46 provided on a side surface, and the through-hole 47 provided at a distal end of the distal end tip 41. The respective through-holes 46 and 47 of the distal end tip 41 function as blood removal holes through which blood can be removed from a blood removal target.

The distal end tip 41 may be made, for example, of hard plastic. By fixing the relatively hard distal end tip 41 to the distal end portion of the first tube 32, it is possible to effectively prevent the entire first tube 32 from being collapsed and blocked by a negative pressure acting on the first tube 32 during the blood removal.

The respective through-holes 46 and 47 of the distal end tip 41 and the blood removing hole 64 of the second tube 33 can be disposed in the different blood removal targets (e.g., the internal jugular vein and the inferior vena cava) of the living body. Therefore, the catheter 60 efficiently performs blood removal through the respective through-holes 46 and 47 and the blood removing hole 64. Further, even if one of the respective through-holes 46 and 47 of the distal end tip 41 or the blood removing hole 64 sticks to the vascular wall or the like and thus is closed, the blood can be removed through the other hole not closed, so that the extracorporeal circulation of the blood can be carried out stably.

As shown in FIG. 3, the lock connector 136 has a first lock connector 137 communicating with the blood feeding lumen 61 of the third tube 34, and a second lock connector 138 communicating with the blood removing lumen 62 of the second tube 33.

The lock connector 136 is a Y-shaped Y connector formed of the first lock connector 137 bifurcated from the second lock connector 138. The blood feeding tube 12 (see FIG. 1) is connected to the first lock connector 137, and the blood removing tube 11 (see FIG. 1) is connected to the second lock connector 138.

Next, the configuration of the dilator 50 will be described.

As illustrated in FIG. 2, the dilator 50 includes a dilator tube 51 provided so as to extend in the axial direction, a dilator hub 52 to which the proximal end of the dilator tube 51 is fixed, and a screw ring 53 provided at a distal end of the dilator hub 52.

The dilator tube 51 is an elongated body extending in the axial direction and having a relatively high rigidity. The entire length of the dilator tube 51 along the axial direction is longer than the entire length of the catheter 60 along the axial direction.

The dilator tube 51 includes a guide wire lumen 54 which allows an insertion of the guide wire (not illustrated). The dilator tube 51 is guided by the guide wire and is inserted into the living body together with the catheter 60. The dilator tube 51 is removed from the catheter 60 by pulling out the dilator hub 52 toward the proximal side after the catheter 60 is indwelled in the living body.

As illustrated in FIG. 2, the distal end of the dilator tube 51 is provided with the flat surface 50a which can be in contact with the receiving surface 48 of the distal end tip 41. The dilator tube 51 has a relatively high rigidity, and has a body which allows a pushing force toward the distal side to be transferred to the distal end tip 41. Therefore, the dilator tube 51 is pushed toward the distal side with the flat surface 50a being in contact with the receiving surface 48 of the distal end tip 41, so that the catheter 60 can be guided to the desired position while widening the relatively thin blood vessel.

As illustrated in FIG. 2, the screw ring 53 of the dilator 50 includes a female screw portion (not illustrated) provided with a screw groove on an inner surface of the lumen. The dilator 50 is configured to be mountable on the catheter 60 by screwing the female screw portion of the screw ring 53 into a male screw portion 138A of the second lock connector 138.

Next, with reference to FIGS. 9 to 13, test results (visual results) of the outflow tests performed on the catheter 60 according to the present embodiment and each of catheters 160 and 260 according to comparative examples will be described.

Figure 9A:
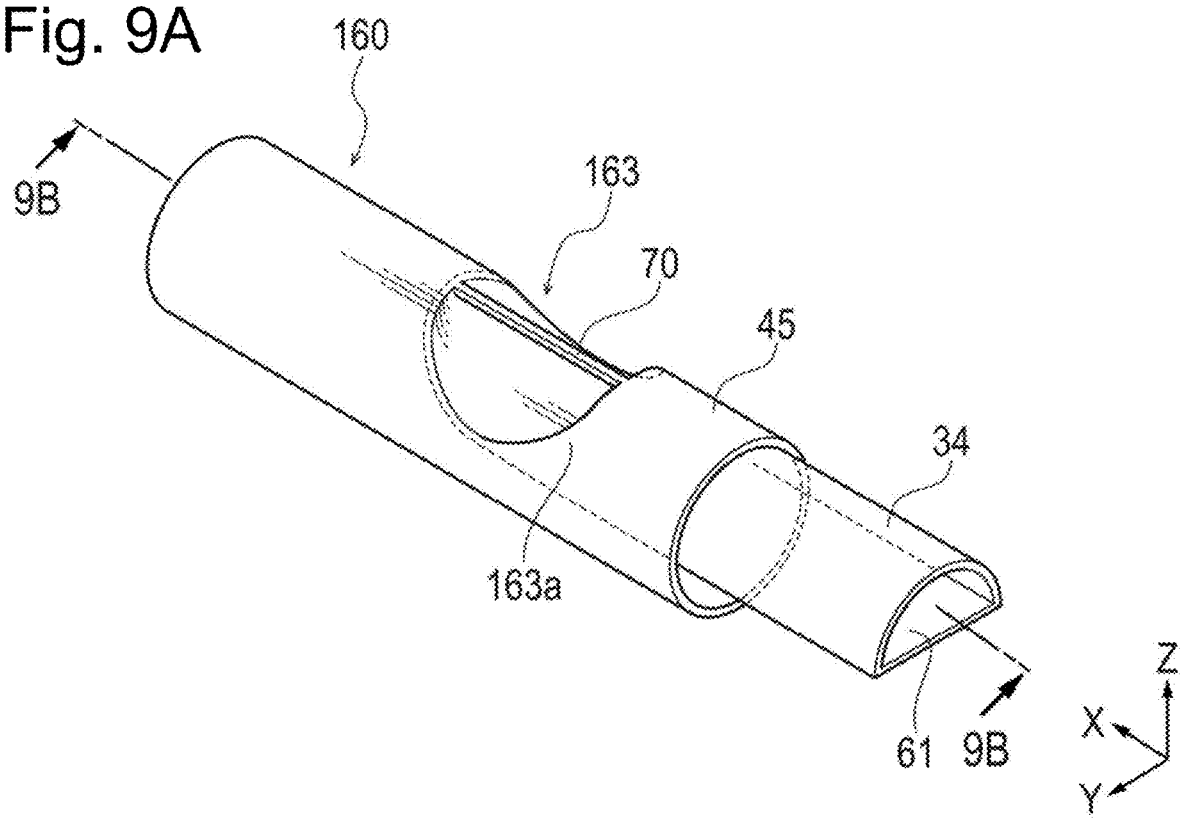
FIG. 9A is a perspective view illustrating a vicinity of a blood feeding hole of a catheter according to a Comparative Example 1 in an enlarged manner.
Figure 9B:
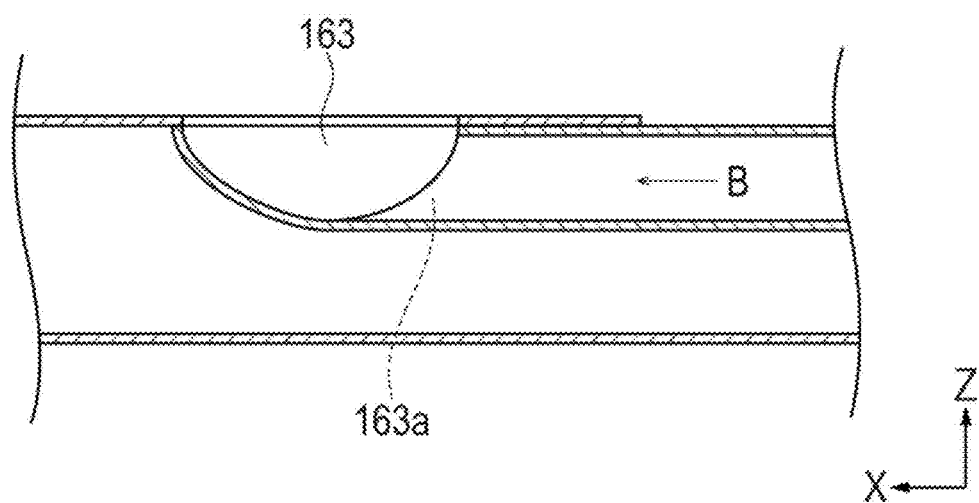
FIG. 9B is a cross-sectional view taken along a line 9B-9B illustrated in FIG. 9A.

A part of the catheter 160 according to Comparative Example 1 is illustrated in FIG. 9A and FIG. 9B. In the catheter 160 according to Comparative Example 1, a side wall 163a is formed at a side portion near the proximal end of a blood feeding hole 163. Note that the catheter 160 is provided with the rib 70.

Figure 10A:
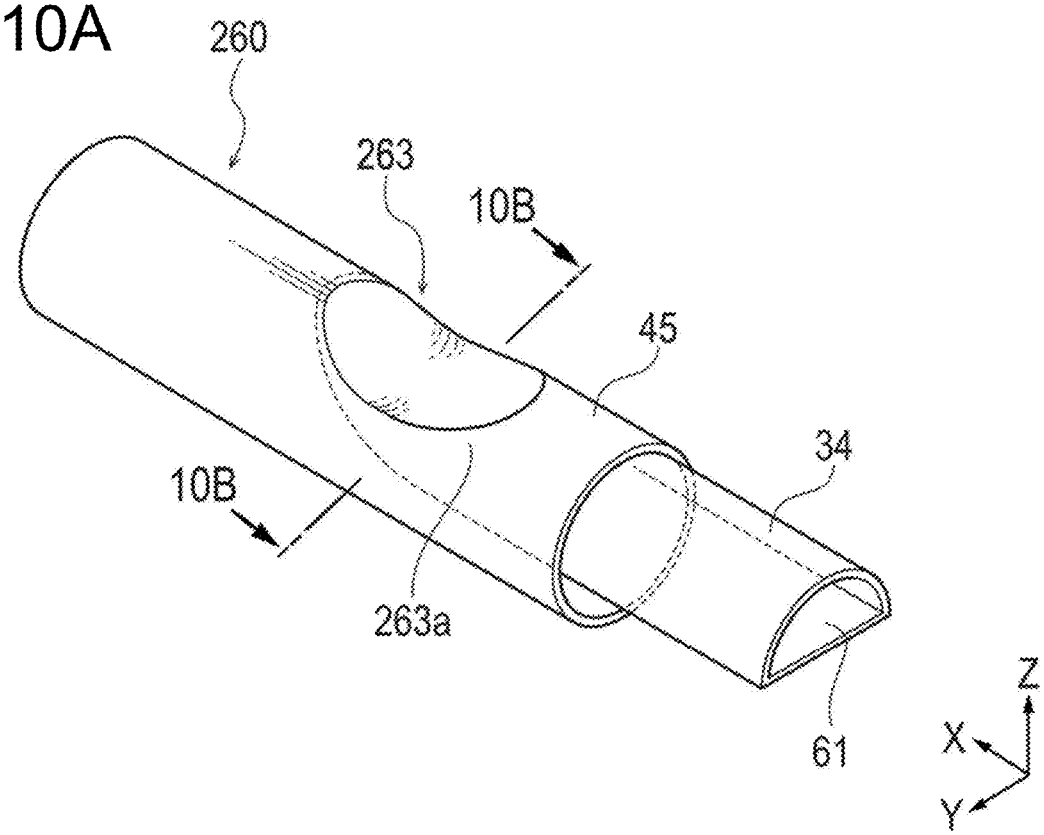
FIG. 10A is a perspective view illustrating a vicinity of a blood feeding hole of a catheter according to a Comparative Example 2 in an enlarged manner.
Figure 10B:
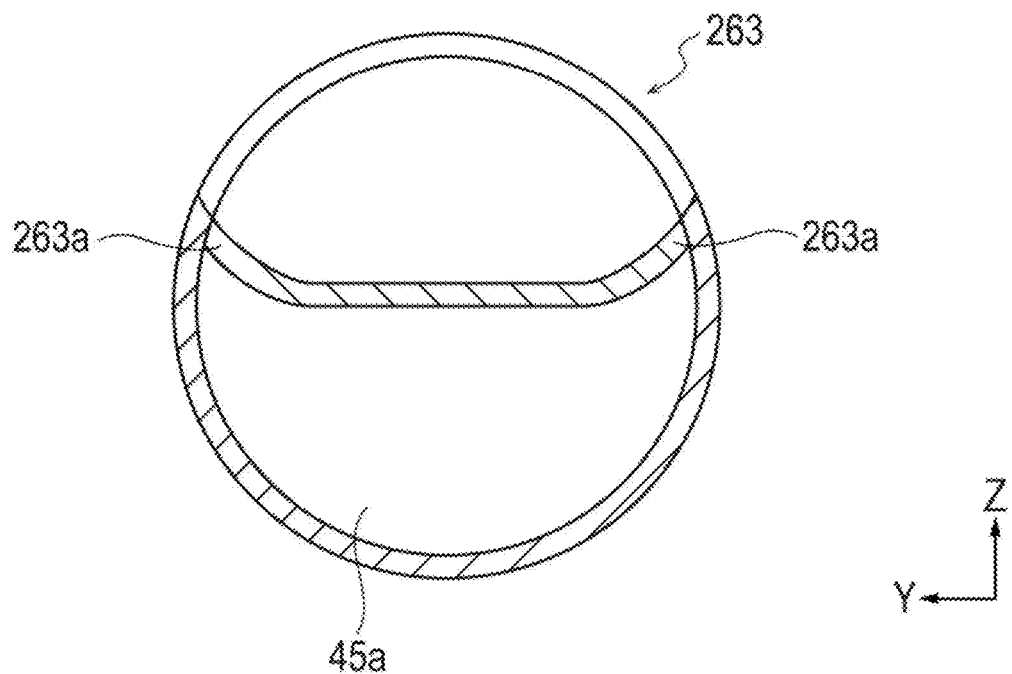
FIG. 10B is a cross-sectional view taken along the line 10B-10B illustrated in FIG. 10A.

A part of the catheter 260 according to Comparative Example 2 is illustrated in FIG. 10A and FIG. 10B. In the catheter 260 according to Comparative Example 2, a side wall 263a is formed at a side portion near the proximal end of the blood feeding hole 163. Further, as illustrated in FIG.

10B, the side wall 263*a* is formed in a shape that rises in the Z direction. The catheter 260 does not have the rib 70.

Figure 11:
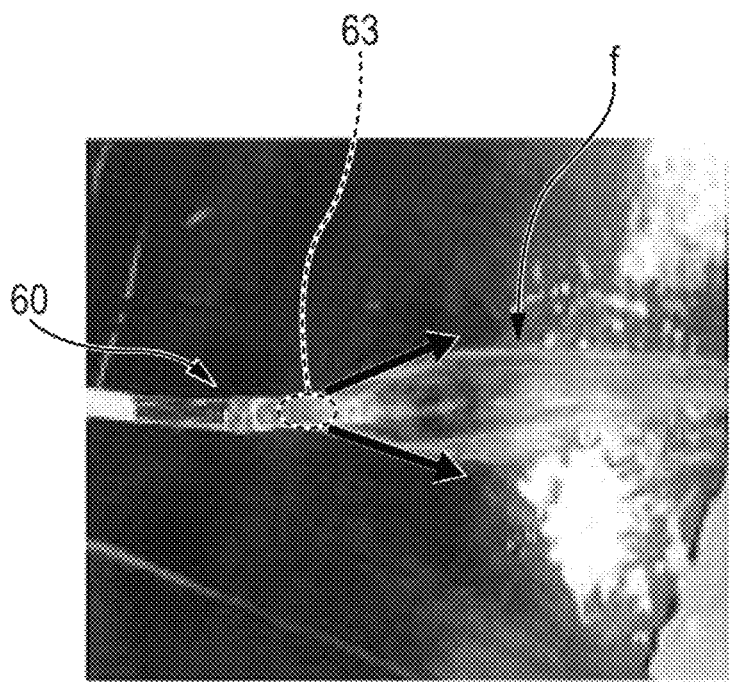
FIG. 11 is a drawing for illustrating results of a catheter outflow test according to the present embodiment.
Figure 12:
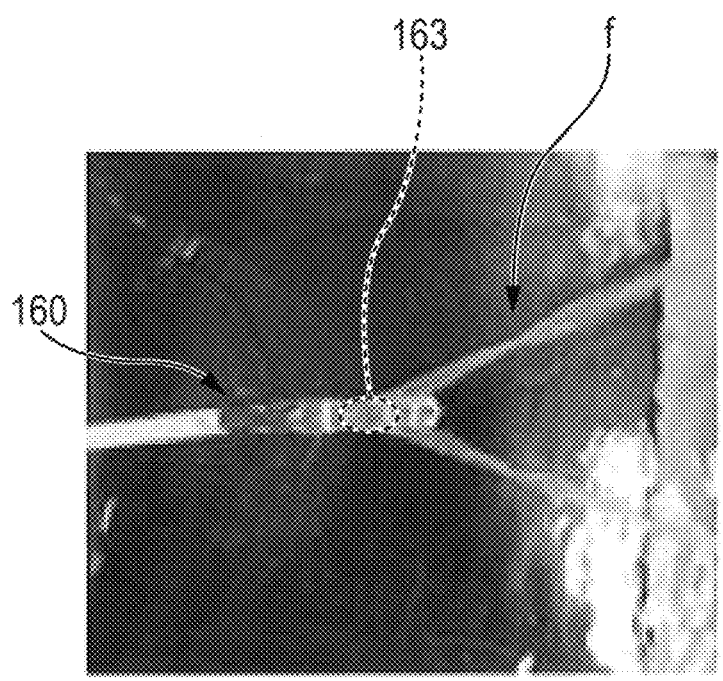
FIG. 12 is a drawing for illustrating results of a catheter outflow test of the catheter according to Comparative Example 1.
Figure 13:
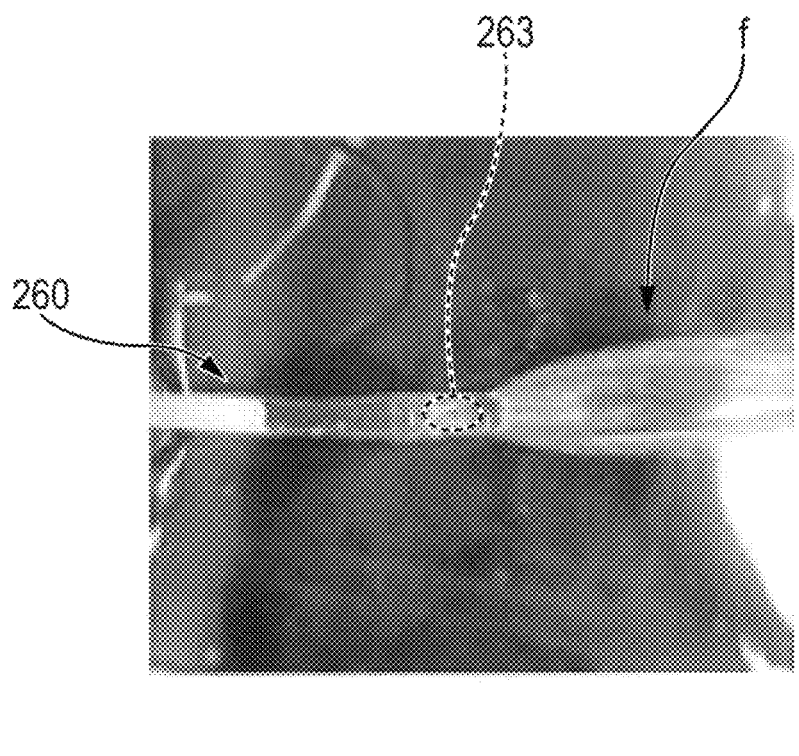
FIG. 13 is a drawing for illustrating results of a catheter outflow test according to Comparative Example 2.

FIG. 11 is a diagrammatic representation of the state in which water is discharged from the blood feeding hole 63 during testing of the catheter 60 according to the embodiment of the present invention. Water was poured into the blood feeding lumen 61 of the third tube 34 at 2 L/min. The view in FIG. 11 is taken from above the catheter 60 (see the plan view illustrated in FIG. 6). FIG. 12 is a diagrammatic representation of the catheter 160 according to Comparative Example 1, which is taken under the same conditions as above, and FIG. 13 is a diagrammatic representation of the catheter 260 according to Comparative Example 2, which is taken under the same conditions as above.

As illustrated in FIG. 11, water f discharged from the blood feeding hole 63 of the catheter 60 according to the embodiment is dispersed toward the outside (a vertical direction in the figure) of the catheter 60. This is considered to be due to the fact that the side wall that prevents the outflow of the water f is not formed at the proximal side of the blood feeding hole 63 connected with the blood feeding lumen 61.

On the other hand, as illustrated in FIG. 12, the catheter 160 according to Comparative Example 1 can be checked as to whether the water f flows linearly toward the distal side (right side in the figure) when the water f flows out from the blood feeding hole 163. This is considered to be due to the formation of the side wall 163*a* which inhibits the dispersion of the water f near the proximal end of the blood feeding hole 163. Also, as shown in FIG. 13, the catheter 260 according to Comparative Example 2 can be checked as to whether the water f is flowing linearly toward the distal side (right side in the drawing) due to the influence of the side wall 263*a* formed near the proximal end of the blood feeding hole 263, in the same manner as in the case of the catheter 160 of Comparative Example 1.

From the above results, it was found that the catheter 60 according to the present embodiment could disperse the outflow of liquid (blood) from the side portion 63*a* near the proximal end of the blood feeding hole 63, thereby reducing the impact of blood collision on the cardiac wall and the like.

The operation and effect of the catheter 60 according to the present embodiment will now be described.

The catheter 60 according to the present embodiment has the blood feeding lumen 61 extending in the axial direction and the blood feeding hole 63 communicating with the distal end of the blood feeding lumen 61, and the side portion 63*a* of the blood feeding hole 63 on the proximal side facing the blood feeding lumen 61 is cut out to the bottom portion 63*b* of the blood feeding hole 63.

In the catheter 60 configured as described above, the blood flowing through the blood feeding lumen 61 reaches the blood feeding hole 63 formed at the distal end of the blood feeding lumen 61, and then flows out of the blood feeding hole 63 while being dispersed. Therefore, the catheter 60 can reduce the impact on the living organs (such as the blood vascular wall and the cardiac wall) caused by the collision of the blood flowing out from the blood feeding hole 63.

The catheter 60 also has the distal wall 63*c*, which is formed at the distal side of the blood feeding hole 63 and curved into a concave shape toward the distal side of the axial direction. Therefore, the catheter 60 can adjust a direction of the blood flowing out to the distal side of the blood feeding hole 63 in a predetermined direction. Further, the distal wall 63*c* is in contact with the blood that flows linearly into the distal side of the blood feeding hole 63 to reduce the force of the blood flow, thereby preventing the blood from sharply flowing out to the distal side of the blood feeding hole 63.

The catheter 60 also has the rib 70 extending between the distal side of the blood feeding hole 63 and the proximal side of the blood feeding hole 63 to prevent the biological tissue from being caught by the blood feeding hole 63. Therefore, the catheter 60 can prevent the biological tissue (such as the wall of the blood vessel) from being caught by the blood feeding hole 63 when the catheter 60 is inserted into the living body, so that insertability into the living body is improved.

Although the catheter according to the invention has been described through the embodiments thus far, the invention is not limited to the configuration described in the embodiments, and may be modified as needed based on the description of the appended claims.

For example, the shape of the blood feeding hole in which the blood flows out from the catheter is not particularly limited as long as the proximal side portion facing the blood supply lumen is cut out to the bottom portion of the blood feeding hole (the side wall which inhibits the outflow of the blood is not formed on the proximal side of the blood feeding hole), and the specific shape (the sectional shape, outer shape etc.), the size, the position, and the like are not particularly restricted.

Figure 14:
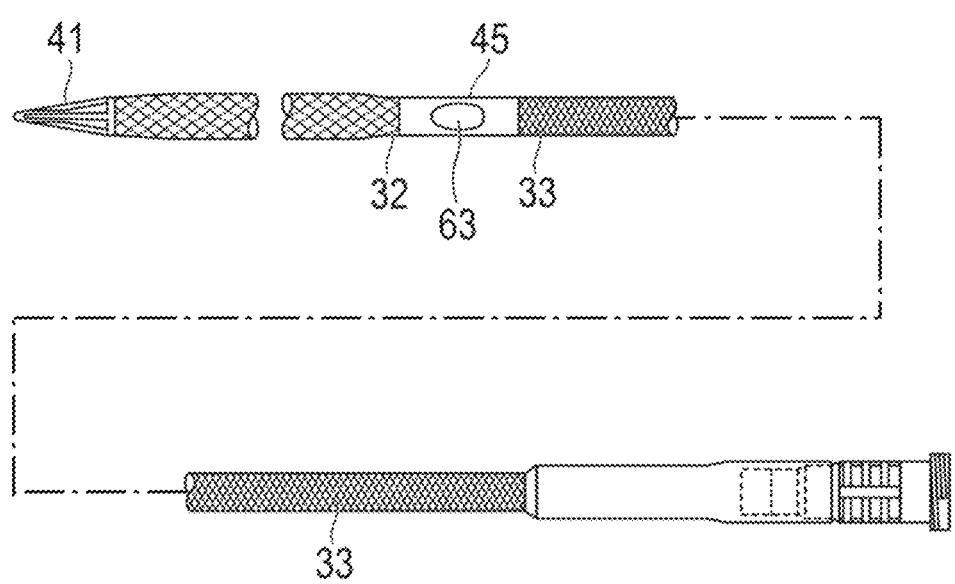
FIG. 14 illustrates a catheter (blood feeding catheter) according to a modified embodiment.

Although the described catheter is a double-lumen catheter which can be used both for blood removal and blood feeding, the catheter may be configured as a blood feeding catheter 60A intended for blood feeding as illustrated in FIG. 14, for example. Note that although the detailed structure of the blood feeding catheter 60A is omitted, it may include, for example, the first tube 32, the second tube 33, the connector 45, or the like. In this case, the blood feeding hole 63 may be formed by a hole (such as a side hole) formed in the connector 45, for example.

The catheter tube of the catheter may also be formed of, for example, one tube, without being formed by a plurality of the tubes, such as the first tube, the second tube, and the third tube. In this case, the provision of the connector 45 may be omitted as appropriate.

What is claimed is:

1. A catheter extending in an axial direction for allowing passage of blood, comprising:
   a tube defining a blood feeding lumen extending in the axial direction; and
   a rigid connector receiving the tube and having a side hole;
   wherein the tube comprises a blood feeding hole at a distal end of the blood feeding lumen cooperating with the side hole to define an opening with a proximal edge facing the blood feeding lumen that is cut out to a bottom portion of the blood feeding hole so that the proximal edge is substantially perpendicular to the axial direction, and wherein the opening has an outer shape decreasing in width from the proximal edge to the distal end of the blood feeding lumen;
   wherein the blood feeding hole comprises a distal wall formed at a distal side of the blood feeding hole as an extension of a bottom planar wall of the tube so as to be curved into a concave shape.

2. The catheter according to claim 1, further comprising a rib extending between the distal side of the blood feeding hole and the proximal edge of the blood feeding hole, configured to prevent a biological tissue from being caught by the blood feeding hole.

3. The catheter according to claim 2, wherein the rib is comprised of a rod-like member extending substantially linearly along the axial direction and is formed by a portion of the connector extending across the side hole.

4. The catheter according to claim 1, wherein the tube has a semi-cylindrical shape on a proximal side from the blood feeding hole.

5. A catheter extending in an axial direction for conveying blood in an extracorporeal blood circulator, comprising:
   a rigid connector having a side hole;
   a first tube with a proximal end connected to a distal side of the connector and a distal end for receiving a blood flow from a living body;
   a second tube with a distal end connected to a proximal side of the connector and a proximal end for coupling the blood flow received from the living body to the extracorporeal blood circulator;
   a third tube installed within the second tube and defining a blood feeding lumen extending in the axial direction, wherein the third tube has a distal end coupled to the connector and a proximal end for receiving a return blood flow from the extracorporeal blood circulator, wherein the distal end of the third tube defines a blood feeding hole in cooperation with the side hole to define an opening with a proximal edge facing the blood feeding lumen that is cut out to a bottom portion of the blood feeding hole so that the proximal edge is substantially perpendicular to the axial direction, and wherein the opening has an outer shape decreasing in width from the proximal edge to a distal side of the blood feeding hole.

6. The catheter according to claim 5, wherein the blood feeding hole further comprises a distal wall formed at the distal side of the blood feeding hole as an extension of a bottom planar wall of the third tube so as to be curved into a concave shape.

7. The catheter according to claim 5, further comprising a rib extending between the distal side of the blood feeding hole and the proximal edge of the blood feeding hole, configured to prevent a biological tissue from being caught by the blood feeding hole.

8. The catheter according to claim 7, wherein the rib is comprised of a rod-like member extending substantially linearly along the axial direction and is formed by a portion of the connector extending across the side hole.

9. The catheter according to claim 5, wherein the third tube has a semi-cylindrical shape on a proximal side from the blood feeding hole.

* * * * *